(12) United States Patent
Swager et al.

(10) Patent No.: US 12,005,014 B2
(45) Date of Patent: Jun. 11, 2024

(54) ASSEMBLY, CONFIGURED TO DETECT A BODY ON A SUPPORT

(71) Applicant: Momo Medical Holding B.V., Delft (NL)

(72) Inventors: Ide Simon Swager, The Hague (NL); Menno Laurens Gravemaker, Delft (NL)

(73) Assignee: Momo Medical Holding B.V., Delft (NL)

( * ) Notice: Subject to any disclaimer, the term of this patent is extended or adjusted under 35 U.S.C. 154(b) by 706 days.

(21) Appl. No.: 16/972,819

(22) PCT Filed: Jun. 6, 2019

(86) PCT No.: PCT/NL2019/050341
§ 371 (c)(1),
(2) Date: Dec. 7, 2020

(87) PCT Pub. No.: WO2019/240569
PCT Pub. Date: Dec. 19, 2019

(65) Prior Publication Data
US 2021/0244349 A1    Aug. 12, 2021

(30) Foreign Application Priority Data
Jun. 11, 2018    (NL) ...................................... 2021099

(51) Int. Cl.
*A61G 7/057*    (2006.01)
*A61B 5/00*    (2006.01)
(Continued)

(52) U.S. Cl.
CPC ............ *A61G 7/057* (2013.01); *A61B 5/0205* (2013.01); *A61B 5/447* (2013.01); *A61B 5/6892* (2013.01); *G04F 1/005* (2013.01); *G06F 3/14* (2013.01); *G08B 7/06* (2013.01); *A61B 5/1115* (2013.01); *A61B 2562/0219* (2013.01); *A61B 2562/0247* (2013.01); *A61B 2562/0252* (2013.01); *A61B 2562/046* (2013.01); *A61G 2205/20* (2013.01)

(58) Field of Classification Search
None
See application file for complete search history.

(56) References Cited

U.S. PATENT DOCUMENTS

| 4,407,587 A | 10/1983 | Fujita |
| 4,995,018 A | 2/1991 | Edwards |

(Continued)

OTHER PUBLICATIONS

WIKIPEDIA, "Piezoresistive effect", captured by the Internet Archive Aug. 14, 2017, 4 pp.

*Primary Examiner* — Etsub D Berhanu
*Assistant Examiner* — Martin Nathan Ortega
(74) *Attorney, Agent, or Firm* — Myers Bigel, P.A.

(57) ABSTRACT

The present invention relates to an assembly, configured to detect a body on a support, comprising: —the support having a body receiving surface configured to receive the body; —an array of sensors that is arranged at a distance relative to the body receiving surface of the support and comprising: —a plurality of presence detectors; —at least one liveliness detector; and —a controller configured to detect the presence of a living person based on measurement signals of both the presence detectors and the at least one liveliness detector.

26 Claims, 7 Drawing Sheets

(51) Int. Cl.
    *A61B 5/0205*     (2006.01)
    *A61B 5/11*     (2006.01)
    *G04F 1/00*     (2006.01)
    *G06F 3/14*     (2006.01)
    *G08B 7/06*     (2006.01)

(56) References Cited

U.S. PATENT DOCUMENTS

| | | |
|---|---|---|
| 6,014,346 A | 1/2000 | Malone |
| 6,646,556 B1 | 11/2003 | Smith et al. |
| 7,027,358 B1 | 4/2006 | Esposito et al. |
| 8,477,036 B2 | 7/2013 | Meyers |
| 8,821,418 B2 | 9/2014 | Meger et al. |
| 2005/0282132 A1 | 12/2005 | Brito |
| 2007/0183269 A1 | 8/2007 | Baba |
| 2007/0272450 A1* | 11/2007 | Skinner .............. A61B 5/1115 177/144 |
| 2008/0130422 A1 | 6/2008 | Hocherman |
| 2009/0209896 A1 | 8/2009 | Selevan |
| 2011/0071482 A1 | 3/2011 | Selevan |
| 2013/0090571 A1* | 4/2013 | Nourani .............. G16H 20/30 600/587 |
| 2014/0039351 A1 | 2/2014 | Mix et al. |
| 2014/0350351 A1 | 11/2014 | Halperin et al. |
| 2015/0300872 A1* | 10/2015 | Hirose .............. G01L 1/04 5/310 |
| 2016/0022218 A1 | 1/2016 | Hayes et al. |
| 2016/0089059 A1* | 3/2016 | Hu .............. A61B 5/7207 600/595 |
| 2016/0302715 A1 | 10/2016 | Larson et al. |
| 2016/0374619 A1* | 12/2016 | Borkholder .......... A61B 5/7246 600/301 |
| 2017/0254059 A1* | 9/2017 | Shen .............. B65F 1/1473 |
| 2018/0020984 A1* | 1/2018 | Hall .............. A47K 13/24 600/301 |
| 2019/0015702 A1* | 1/2019 | Krebs .............. B64G 1/66 |

* cited by examiner

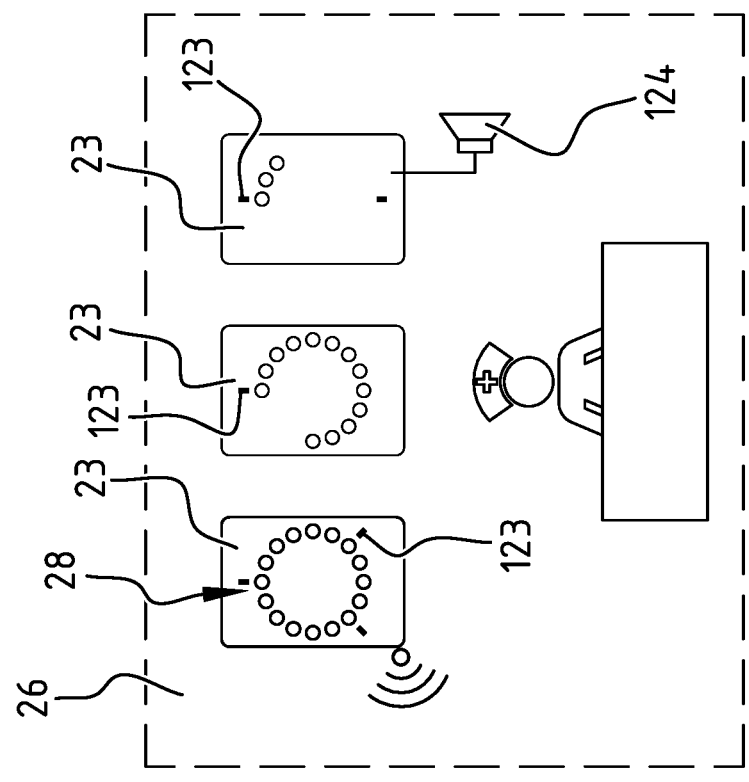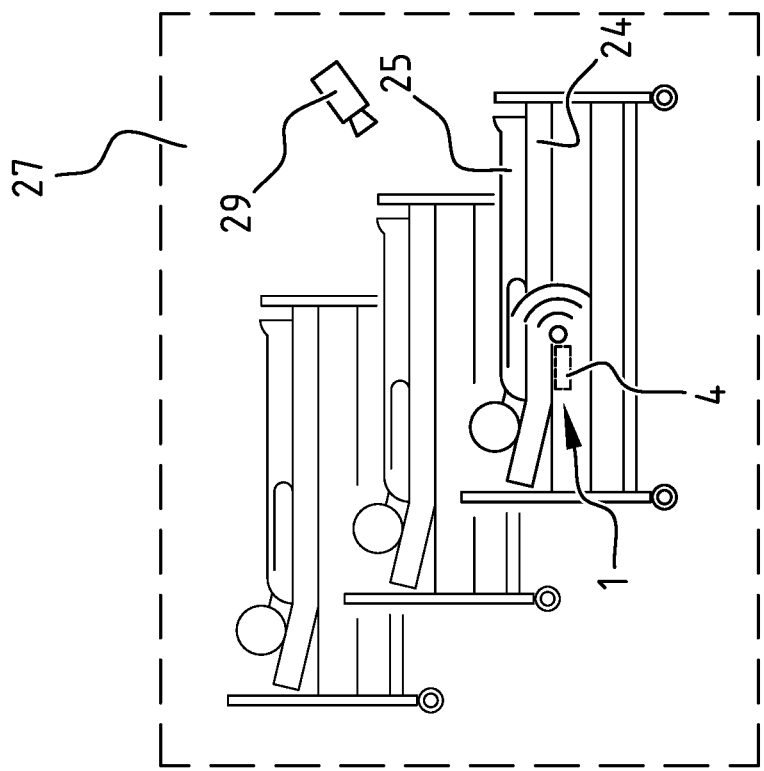
FIG. 4

ASSEMBLY, CONFIGURED TO DETECT A BODY ON A SUPPORT

The present invention relates to an assembly, configured to detect a body on a support.

Pressure ulcers, also known as pressure sores, pressure injuries, bedsores, and decubitus ulcers, are localized damage to the skin and/or underlying tissue resulting from prolonged pressure on the skin. The pressure may be in combination with shear and/or friction.

People most at risk of pressure ulcers are those with a medical condition that limits their ability to change posture or those who spend most of their time in a bed or (wheel) chair. Besides the patients suffering, pressure ulcers may also lengthen the time period patients are hospitalized, thereby increasing healthcare costs.

The best way to prevent pressure ulcers is by regularly changing the posture of the patient, also referred to as repositioning. However, in practice this method leads to either undertreatment or overtreatment. This is caused by lack of information about the posture and movements of the patient over time. On the one hand, when repositioning is not done often enough, the chances are high that a pressure ulcer will develop. Pressure ulcers can develop within hours in weak patients. On the other hand, when repositioning is done too often, this takes up valuable time of the nurse and causes inconvenience to the patient.

Current solutions are not able to solve these problems adequately. Awareness campaigns and manual administration lists have been used for decades but are not effective in the long run. Active air mattresses help by equalizing the pressure across the body, but repositioning is still needed.

Some sensor systems are available, and they are mostly targeted at bed exit and movement detection. Such sensor systems are arranged on top of a mattress, and may therefore be felt by the patients, which is undesirable. In extreme situations, such sensor systems may even increase pressure applied on the skin, increasing the need for repositioning. Other sensors may be attached to the human body, which is undesirable for patients and many end-users.

United States patent application US 2014/0350351 A1 discloses a patient-monitoring system that comprises a plurality of clinical sensors to measure clinical parameters of the patient. It is designed to alert a subset of a plurality of clinicians in response to a measured clinical condition.

United States patent application US 2016/0302715 A1 also describes a patient-monitoring system that is, like the present invention, especially suitable for preventing pressure-induced ischemia, pressure ulcers, pneumonia and other medical conditions. It proposes the use of a mattress with a plurality of sensor build inside said mattress.

Both US 2014/0350351 A1 and US 2016/0302715 A1 fail to disclose a system that is capable to determine the posture of the patient, as well as changes thereto, i.e. repositioning of the patient.

United States patent application US 2016/0022218 A1 discloses to a patient support with patient information sensors, such as a scale to weigh the weight of the person over time.

United States patent application US 2014/0039351 A1 discloses a sensing system for a patient support that includes a flexible sheet that houses a sensor array that detects interface pressures between the patient and the support surface on the patient support. The sensor sheet is arranged on top of the support surface, i.e. between the patient support and the patient, and will therefore be seen and felt by the patient.

There is a need for a patient monitoring system capable of determining the posture of the patient, as well as changes thereto, i.e. repositioning of the patient. Disadvantages of such prior art patient monitoring systems relate to these prior art systems often requiring dedicated supports, such as the mattress with build in sensors of US 2016/0302715 A1. There is a need for a patient monitoring system that may be easily added to an existing patient support, e.g. arranged retrofit to a patient's bed. On the other hand, it is also desirable if the patient monitoring system may be arranged out of sight of the patient in a way that it is also not felt, while still offering accurate measurements.

An object of the present invention is to provide an assembly configured to detect a body on a support, that is improved relative to the prior art and wherein at least one of the above stated problems is obviated.

Said object is achieved with the assembly configured to detect a body on a support, according to the present invention, comprising:
- the support having a body receiving surface configured to receive the body;
- an array of sensors that is arranged at a distance relative to the body receiving surface of the support and comprising:
- a plurality of presence detectors;
- at least one liveliness detector; and
- a controller configured to detect the presence of a living person based on measurement signals of both the presence detectors and the at least one liveliness detector.

By combining measurement signals of both a presence detector and a liveliness detector, it is possible to accurately predict if a living human body is supported by the support. The support is typically a bed, especially a bed in a hospital or other health care center.

Accurate prediction is obtained, because for example a heavy bag may activate the presence detector, but will not activate the liveliness detector. On the other hand, a liveliness detector in the form of a heart rate sensor may erroneously interpret a repetitive signal as a heart rate. For example, piling activities on a building site near a hospital have caused errors in heart rate monitors before. The chance that both a presence detector and a liveliness detector are mistaken at the same time is very low, and limited to extremely rare and specific situations. Therefore, an improved accuracy is obtained by combining measurement signals of both a presence detector and a liveliness detector.

Although the present invention is specifically aimed at, and described in relation to preventing pressure ulcers, an assembly configured to detect a body on a support, that comprises at least one presence detector, at least one liveliness detector, and a controller configured to detect the presence of a living person based on measurement signals of both the at least one presence detector and the at least one liveliness detector, may have many other useful applications. For example, incorporated in a driver's seat of a car, the controller may respond to a heart attack or unconsciousness of the driver by activating an autonomous driving mode to safely stop the car at an emergency lane or other safe place. Emergency services may be automatically informed, and a traffic accident may even be prevented.

An assembly as mentioned above may also be used in a triage process, wherein it is decided in which order patients should be treated first based on how sick or seriously injured they are. The assembly may distinguish between patients who have left the bed or stretcher (no presence nor liveliness is detected anymore), patients who have passed away (presence detected, but no liveliness is detected anymore), and patients who are alive and present. In situations with many casualties that need first aid, such as after a natural disaster or in a war situation or after terroristic attacks, the assembly according to the invention may facilitate the process of prioritizing.

The array of sensors is arranged at a distance relative to the body receiving surface of the support, allowing the array of sensors to be arranged out of sight, e.g. under or in a mattress, at a distance where it is not or hardly felt by a person supported by the support. Nevertheless accurate measurements may still be obtained by using the array of sensors. After all, the array of sensors comprising a plurality of presence detectors and at least one liveliness detector provides the opportunity to accurately measure repositioning, i.e. a person changing posture, and may even determine body posture. Body posture may relate to determining of a person is lying on his/her back, or any of the sides. In fact, it is even possible to determine on which side, i.e. left or right, a person is lying.

According to a preferred embodiment, the at least one presence detector comprises a piezo-resistive sensor. With a piezo-resistive sensor, pressure/weight can be accurately measured. Under ideal conditions, some piezo-resistive sensors 6 may even be able to sense a breathing pattern.

According to a further preferred embodiment, the at least one liveliness detector comprises a piezo-electric sensor, piezo-electric sensors exhibit near zero deflection, and therefore respond across a fairly high-frequency bandwidth and exhibit consistent linearity over a wide amplitude range. Piezo-electric sensors are capable of measuring a heart rate pattern and/or breathing pattern.

According to an even further preferred embodiment, the liveliness detector is configured to determine if a body is lying on a left side or on a right side of the body. In order to be able to do this, the liveliness detector may comprise both a heart rate sensor and a breathing sensor, and may be configured to measure both a heart rate pattern and a breathing pattern, wherein the controller is further configured to determine from the heart rate pattern and the breathing pattern on which side a living person is lying. As the heart is positioned asymmetrical in the body, i.e. for most people in the left body half, the amplitude of the heart rate will be different for a person lying on its left side (with the heart relatively close to the liveliness detector) compared to a person lying on its right side (with the heart relatively far away from the liveliness detector). For a person lying on its left side, the signal of the heart rate will be more clearly present.

According to an even further preferred embodiment, the controller is configured to determine a ratio between an amplitude of the heart rate pattern and an amplitude of the breathing pattern to determine on which side the living person is lying. If the controller is configured to determine a ratio between the amplitude of the breathing pattern and the amplitude of the heart rate pattern over time, it is possible to accurately determine if a body is lying on its left or right side, and when changes are made to the posture.

According to an even further preferred embodiment, the assembly comprises a concentrator that is configured to concentrate a load on the presence detector. Due to the load concentration of the load on the presence detector, the assembly may be arranged at a distance relative to the body receiving surface of the support, whereas an accurate measurement is obtained. For example, the array of sensors may be, relative to the body receiving surface of the support, arranged at an opposite side of the support. It is thus possible to arrange a measurement device under a mattress while still obtaining accurate measurements with respect to body posture and change thereof. The array of sensors may be arranged out of sight, e.g. under a mattress. Although the array or sensors is not felt by a person supported by the support, accurate measurements may still be obtained.

According to an even further preferred embodiment, the concentrator comprises a pivot that is configured to pivotably arrange said concentrator in a measurement device. If the pivot is arranged at a first side of the concentrator and the contact portion is arranged at a lever distance from the pivot, said lever distance provides an amplification of a compressive force acting on the concentrator. In this embodiment, the concentrator not only concentrates the load on the presence detectors, but also amplifies this load. This results in a more sensitive measurement of the presence detectors, allowing for accurate measurement even when the support is a relatively thick mattress. From the examples above, it is clear that an assembly according to the invention may have many useful applications. However, in the remainder of this application, the focus will be on applications to prevent pressure ulcers.

Preferred embodiments are the subject of the dependent claims.

In the following description preferred embodiments of the present invention are further elucidated with reference to the drawing, in which:

FIG. 4 is a schematic figure showing an assembly with a time indicator;

Figure 1:
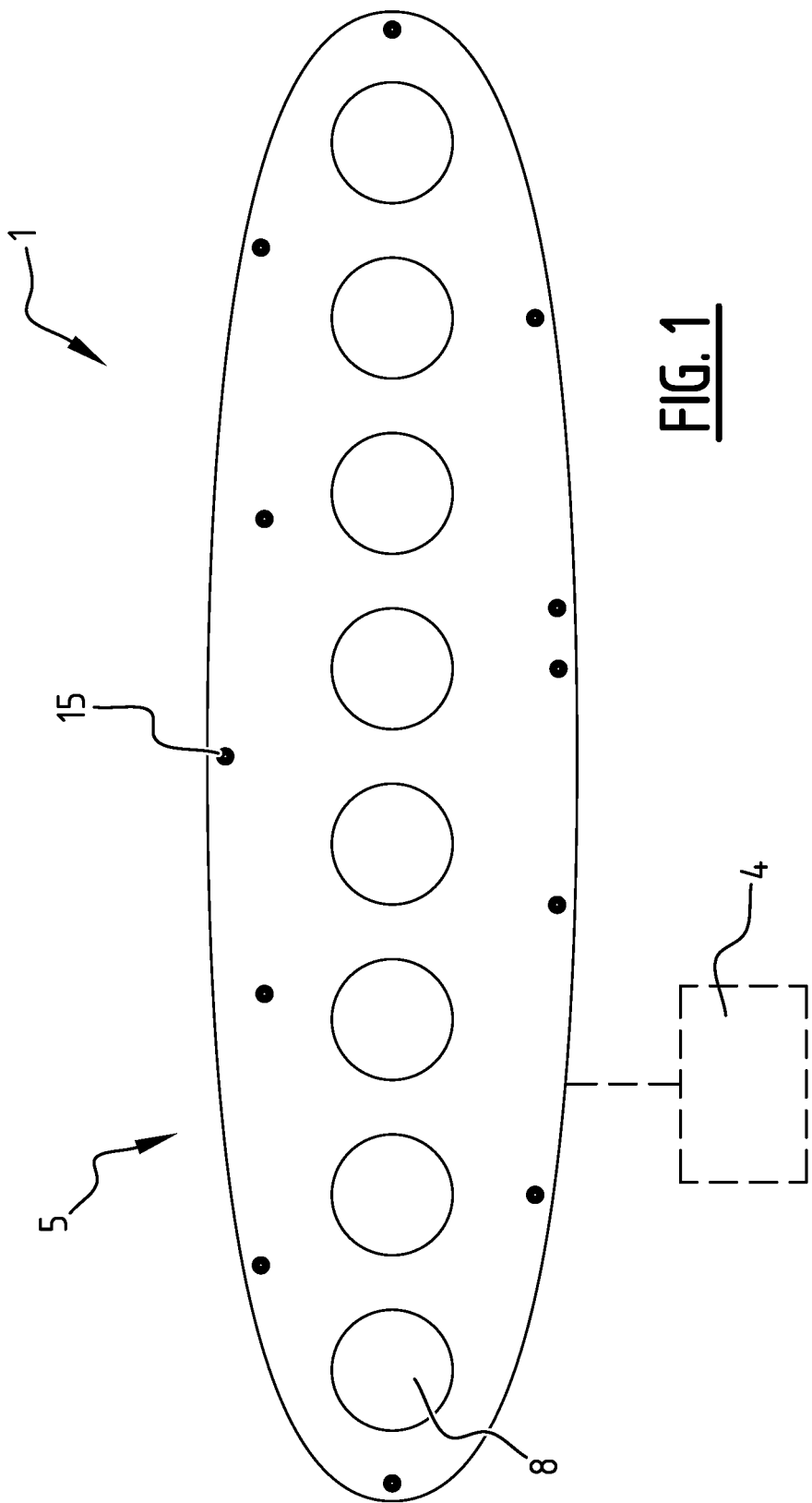
FIG. 1 is a top view of an assembly according to a first preferred embodiment of the invention.
Figure 2:
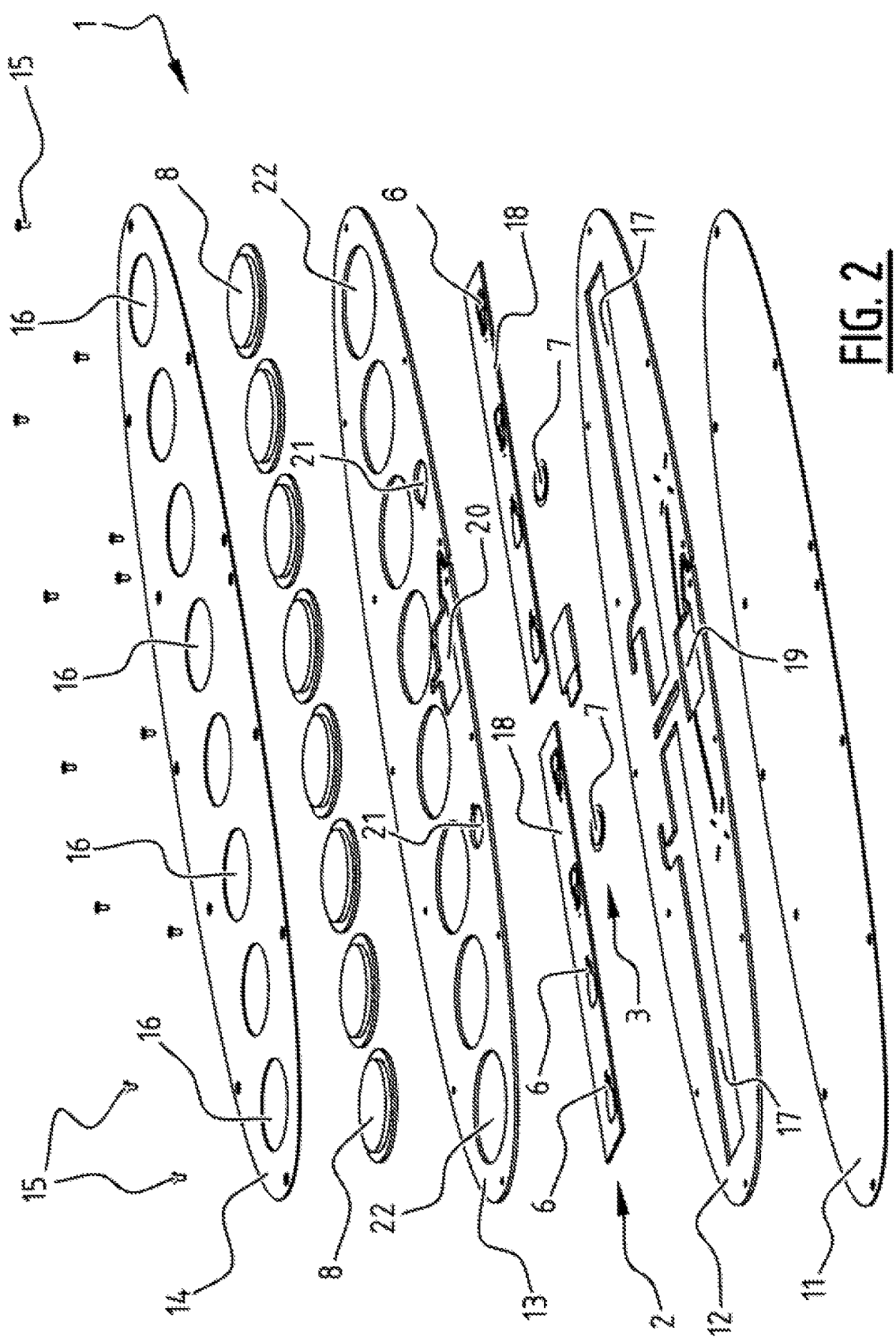
FIG. 2 is an exploded perspective view of the assembly of FIG. 1.

The assembly 1, configured to detect a body on a support, comprises at least one presence detector 2 and at least one liveliness detector 3, as well as a controller 4 configured to detect the presence of a living person based on measurement signals of both the at least one presence detector 2 and the at least one liveliness detector 3.

The support may be a bed having a mattress (not shown), wherein the at least one presence detector 2 is arranged under the mattress. More in particular a measurement device 5 of the assembly 1 may be arranged below the mattress and still accurately predict a posture of a person supported by said support. Contrary to most prior art sensor systems, which are mostly targeted at bed exit and movement detection, the present invention can determine the actual posture the patient is lying in. By obtaining information on posture over a time period, it is possible to accurately determine the need for repositioning required for preventing pressure ulcers.

Although the assembly 1 of the shown embodiment comprises two liveliness detectors 3 arranged in measurement device 5, the skilled person will understand that the liveliness detectors 3 may also be external from the device 5. For example, in a hospital situation, the liveliness detector may comprise an already present monitoring system, such as an ECG-system that is connected to a patient's body. Also, the controller 4 may be external from measurement device 5, as indicated in FIG. 1. Communication between the measurement device 5 and the controller 4 may be either by wire (as shown), or wireless.

The at least one presence detector 2 comprises at least one of a pressure sensor and a weight sensor, which is in the Figures indicated as a presence sensor 6. In the shown embodiment, the at least one presence detector 2 comprises a piezo-resistive sensor 6. In a piezo-resistive sensor 6, pressure or mechanical stress results in a change in resistance across the piezo material. With a piezo-resistive sensor 6, pressure/weight can be accurately measured. Under ideal conditions, some piezo-resistive sensors 6 may even be able to sense a breathing pattern.

The at least one liveliness detector 3 comprises at least one of a heart rate sensor and a breathing sensor, in the Figures both indicated as a liveliness sensor 7. As indicated above, the liveliness detector 3 may comprise an already present monitoring system, such as an ECG-system that is connected to a patient's body in a healthcare situation. In the shown embodiment, the at least one liveliness detector 3 comprises a piezo-electric sensor 7. A piezo-electric sensor 7 converts mechanical energy, such as pressure or mechanical stress, to electrical energy. As they exhibit near zero deflection, they respond across a fairly high-frequency bandwidth and exhibit consistent linearity over a wide amplitude range. Piezo-electric sensors 7 are capable of measuring a heart rate pattern H and/or breathing pattern B. The at least one liveliness detector 3 may also comprise a force sensing sensor of a different type than a piezo-electric sensor 7, such as a force sensing resistor.

The shown presence detector 2 is configured to determine if a body is lying on the back or on any of the sides. In order to be able to discriminate between these postures, the presence detector 2 of the shown embodiment comprises an array of piezo-resistive sensors 6. If a body is lying on the back, the array of piezo-resistive sensors 6 measures a more or less uniform pressure pattern. However, if a body is lying on one side, the pressure pattern will show a higher peak pressure due to the weight being distributed over a smaller contact area between the body and the mattress. In general, the pressure level will more gradually decrease away from the body at the front side of the body, than away from the back side of the body. The pressure measurement provided by the array of piezo-resistive sensors 6 may thus give an indication if a person is lying on the left or right side of the body.

In order to further increase the accuracy of predicting on which side a body is lying, the liveliness detector 3 is preferably configured to measure both a heart rate pattern H and a breathing pattern B, and the controller 4 is further configured to determine from the heart rate pattern H and breathing pattern B on which side a living person is lying.

The liveliness detector 3 of the shown embodiment comprises two piezo-electric sensors 7, which is the minimum number required to allow the assembly to determine both the location of the body on the support 24 and the posture of said body on the support 24.

The position of the body may be determined by comparing the output of both piezo-electric sensors 7 of the liveliness detector 3. Most accurate prediction may be obtained if the piezo-electric sensors 7 are arranged in the area where the heart and lungs of the body are located, and if they are substantially arranged at the same height along the length of the body. In practice, the piezo-electric sensors 7 are preferably located on a left and right side of the support 24. The controller 4 may be configured to determine the difference in overall amplitudes of the measurement signal of both piezo-electric sensors 7. The piezo-electric sensor 7 that carries most of the body weight gives an indication where the body is positioned. Body position, besides being useful for pressure ulcer prevention, may also be used for fall prevention. After all, the controller 4 may notice a body moving too far towards an edge of the support 24, and provide an alarm before the person falls off the support 24.

Figure 5:
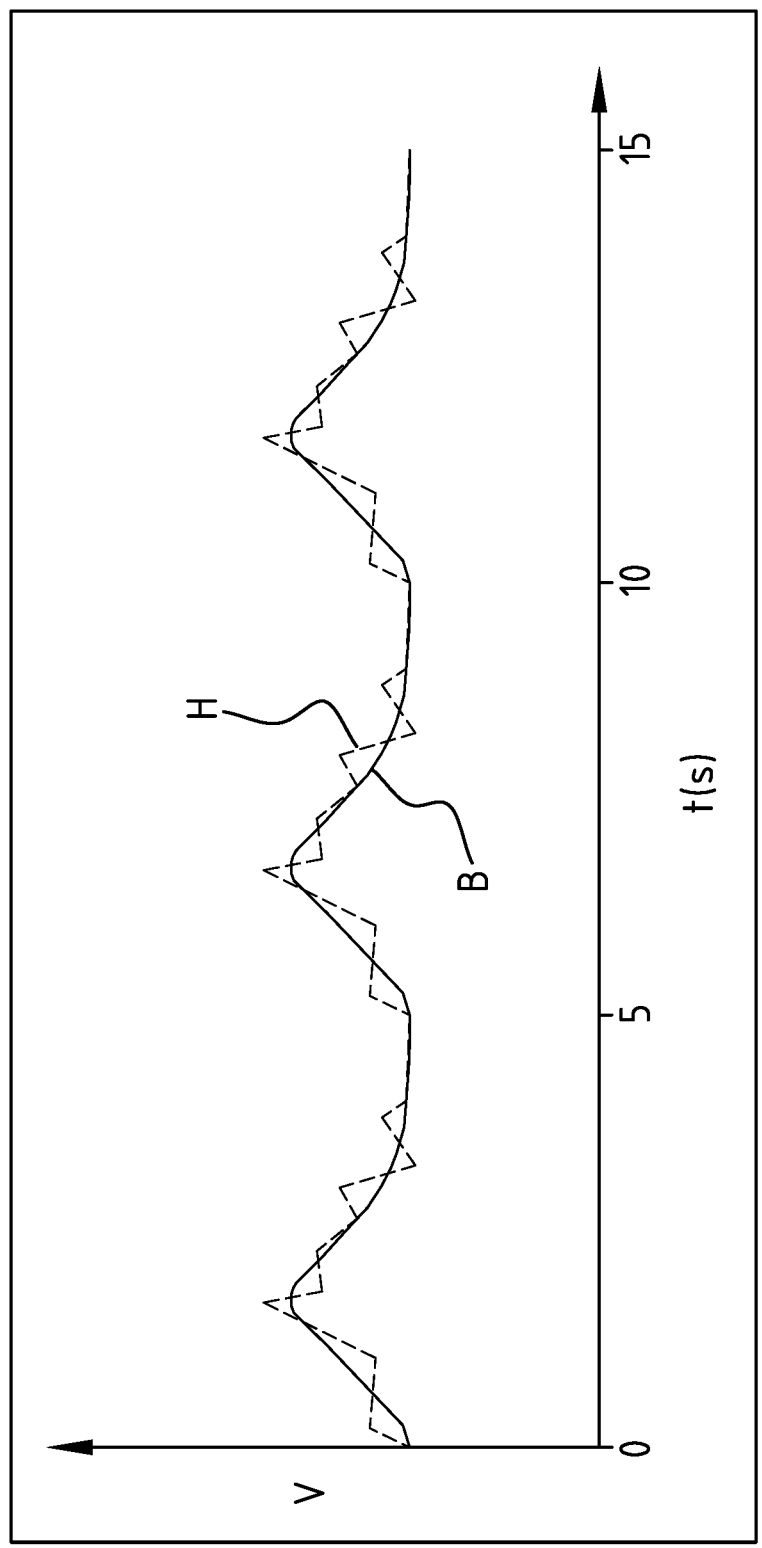
FIG. 5 is a measurement signal of a piezo-electric sensor of a liveliness detector.

The posture of the body may be accurately determined by the controller 4 based on measurement data of at least one piezo-electric sensor 7 of the liveliness detector 3. As mentioned above, the piezo-resistive sensors 6 of the presence detector 2 may accurately determine if a person is lying on the back or on one of the sides. Moreover, the piezo-resistive sensors 6 may also give an indication if the person is lying on its left or right side, but this indication is not always very accurate. Using a piezo-electric sensor 7 of the liveliness detector 3 it may be far more accurately predicted if a person is lying on the left or right side of the body. The controller 4 preferably first determines which one of the piezo-electric sensors 7 of the liveliness detector 3 provides the most suitable measurement signal, e.g. which piezo-electric sensor 7 carries most of the body weight at that time. The controller 4 then analyses the measurement signal of (a selected) one of the piezo-electric sensors 7 of the liveliness detector 3 over time. A piezo-electric sensor 7 may measure multiple biological signals (respiration/heartbeat/etc.), and thus the piezoelectric signal may be used to determine characteristics (like amplitude/RMS/power/energy/frequency/phase/etc.) of these signals relative to each other and themselves over time. The piezo-electric sensor 7 will output a Voltage, and will typically provide a measurement signal as shown in FIG. 5. The breathing pattern B of e.g. one breath every five seconds provides a first sinusoidal-like pattern and has a significantly larger amplitude (i.e. variation) than the amplitude (i.e. variation) of the heart rate pattern H. At a resting heart rate of sixty beats per minute, there are about 5 heart beats during one breathing cycle. As the heart is positioned asymmetrical in the body, i.e. for most people in the left body half, the amplitude of the heart rate will be different for a person lying on its left side (with the heart relatively close to the piezo-electric sensor 7) compared to a person lying on its right side (with the heart relatively far away from the piezo-electric sensor 7). For a person lying on its left side, the signal of the heart rate will be more clearly present. Thus, if the controller 4 is configured to determine a ratio between the amplitude of the breathing pattern B and the amplitude of the heart rate pattern H over time, it is possible to accurately determine if a body is lying on its left or right side, and when changes are made to the posture.

The assembly 1 may further comprise an inclination sensor 10 that is configured to measure an inclination of the support. Based on the inclination, the controller 4 is able to more accurately determine the pressure on the skin that may cause pressure ulcers. The inclination sensor 10 may comprise an accelerometer.

The measurement device 5 of the assembly 1 comprises a bottom layer 11, a lower mid layer 12, a top mid layer 13, and a top layer 14, assembled using a plurality of screws 15. The bottom layer 11 and top layer 14 provide a smooth outer surface of the measurement device 5. Holes 16 in the top layer 14 expose a number of dome shaped concentrators 8. The lower mid layer 12 comprises accommodations 17 configured to accommodate one or more than one printed circuit board 18. Accommodation 19 in the lower mid layer 12 and accommodation 20 in the top mid layer 13 provide an accommodation space for the inclination sensor 10. The top mid layer 13 further comprises two accommodations 21 for the liveliness sensors 7 of the liveliness detector 3. Finally, the top mid layer 13 further comprises eight accommodations 22 for the concentrators 8.

The measurement device 5 of the assembly 1 comprises an array of eight presence sensors 6. In the shown embodiment, near each presence sensor 6 there is provided a concentrator 8 that is configured to concentrate a load on the presence sensor 6.

Preferably, the concentrator 8 is further configured to unload the presence sensor 6 in an unoccupied state of the support. This prevents the assembly 1 from having to be calibrated before every use. It suffices if the presence sensors 6 are calibrated once. e.g. in the production process.

Figure 3:
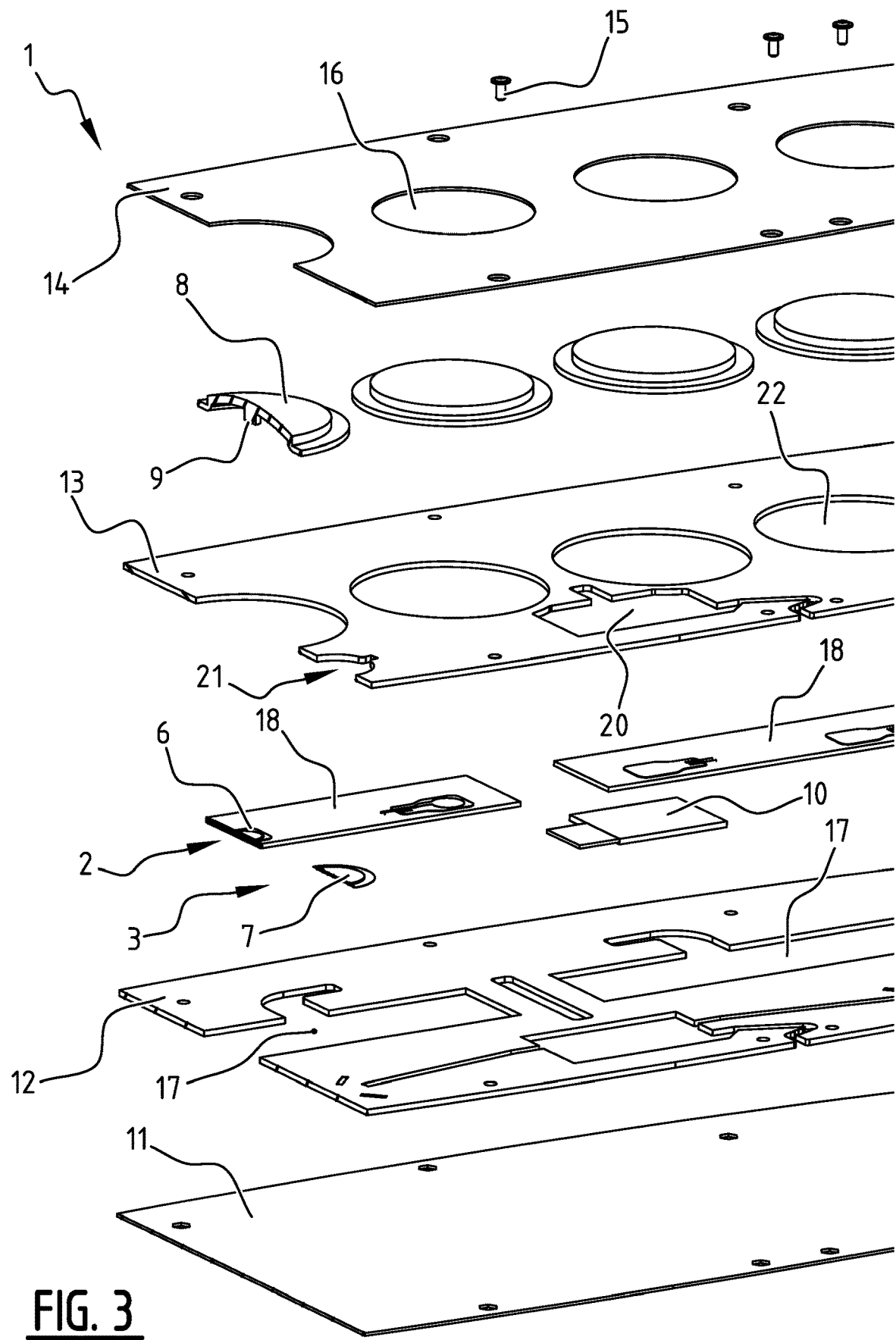
FIG. 3 is a detailed cross-sectional exploded view of FIG. 2.

As can be best seen in the cross-sectional view of FIG. 3, the concentrator 8 extends over the at least one presence sensor 6. The concentrator 8 is moveable relative to the presence sensor 6 and is preferably resilient. i.e. it be made of a resilient material and/or comprises resilience due to its mechanical construction. For example, it may comprise at least one living hinge (not shown). Alternatively, the concentrator may be moveable relative to the presence sensor 6 in a pivotable arrangement as shown in the second preferred embodiment of FIGS. 6 and 7.

The shown concentrators 8 comprise a dome shape, allowing it to concentrate a force applied to a relatively large area of the support 24, e.g. a mattress, on the dedicated presence sensor 6.

In order to enhance force transfer between the concentrator 8 and the presence sensor 6, the concentrator 8 may comprise a contact portion 9 that is configured to abut the sensor 6 of the presence detector 2 when a body is present on the support. The contact portion 9 is preferably a rigid portion.

The concentrator 8 is configured to have the contact portion 9 arranged at an offset relative to the sensor 6 of the presence detector 2 below a predetermined unoccupied load that is more than the load of an unoccupied support.

The concentrator 8 is further configured to have the contact portion 9 arranged in abutment with the sensor 6 of the presence detector 2 above a predetermined occupied load, that is less than or equal to the load of a support occupied by a human body.

As schematically shown in FIG. 4, the assembly may further comprise a time indicator 23 configured to indicate a time lapsed since a preceding event or a time remaining up to a subsequent event. The preceding and subsequent events may be related to a necessity of a patient changing position/posture, but may also be used for other purposes, where regular checks on a person, patient or animal are desired at fixed intervals (the maximum period between a preceding event and a subsequent event), for example in relation to timely and/or regular medicine administration or the like.

The time indicator may have an incorporated controller and be arranged at a side of a bed, or may have a remote controller at a control room while the time indicator is at a bed side, or the entire time indicator may be arranged at the control room or be (part of) a console to monitor more locations of events occurring.

The time indicator 23 has a display to output an indication of lapsed or remaining time, relative to a maximum period of time. However, the output indication is not necessarily displayed in terms of actual or real time in time units such as minutes, as will be explained below.

The controller 4 may be further configured to reset the time indicator 23 if at least one or both of the at least one presence detector 2 and the at least one liveliness detector 3 detects that the body 25, that is lying on the support 24, i.e. the mattress in FIG. 4, is changing posture.

The time indicator 23 may be arranged remote from a location 27 of the support 24 and assembly 1, preferably in a different room, such as a control room 26. From this control room 26, healthcare personnel may monitor multiple time indicators 23 that each indicate time lapsed since an event, such as a specific patient having moved to another posture, or a time to such an event.

Too many alarms may cause "alarm fatigue", which is a sensory overload when healthcare personnel is exposed to an excessive number of alarms. Alarm fatigue can result in desensitization to alarms and missed alarms. Patient deaths have been attributed to alarm fatigue, which is therefore a major concern for patient safety. The time indicator 23 according to the invention may be used to present information of an upcoming event, such as a not so urgent repositioning activity, to healthcare personnel in a non-intrusive way. More in particular, the time indicator 23 provides healthcare personnel with information that allow them to pro-actively plan their work, rather than re-actively responding to displayed, auditory or even tactile alarms. This planning contributes to a patient being moved to another position in time, thereby reducing the risk of pressure ulcers being formed. Nevertheless, the time indicator may comprise or be connected to an alarm to warn nursing staff that for a particular individual the maximum period is about to end or has ended. In FIG. 4 the alarm is in the exemplary embodiment of a loudspeaker 124.

Although the time indicator 23 may be a "real" timer, such as a countdown timer showing the minutes remaining till an event in digits, it is preferred that the time indicator 23 provides a visual indication 28 of the time lapsed since an event or a time to an event. Such a visual indication, which may comprise a graphical representation of the time lapsed since the event or a time to the event, is easy to monitor. In FIG. 4, the time indicator 23 comprises a series/array of lights that gradually in- or decreases till it represents a full or empty circle (depending on a mode of counting up lapsed time, or a mode of counting down remaining time of the maximum period). Also the color of the lights may change. The controller 4 may be configured to drive the display of the time indicator 23 to output any one or more than one from the group of: a background of the indication of lapsed or remaining time of the maximum period; an illumination of a housing of the time indicator; and the indication of lapsed or remaining time of the maximum period, in a color corresponding with proximity to an end of the maximum period. More in particular, output of a green or blue color may indicative of an end to the maximum period being remote: a yellow or orange color may be indicative of an end to the maximum period being close; and a red color may be indicative of the maximum period having ended. Of course, many forms are possible: the lights may also decrease to represent a countdown timer. Instead of shown discrete lights, the lights may also be embodied as a continuous bar. Instead of the circular shape, other shapes such as straight bars or even a pie diagram may be applied.

In the example of FIG. 4, a front display of the time indicator 23 may therefore comprise a plurality of light sources in an array, wherein the controller 4 may be configured to sequentially light up or extinguish light sources in the array in correspondence with lapsed or remaining time relative to the maximum period. The array may be arranged in a circular, clock-like configuration, and a full length of the array may correspond with the maximum period.

The display of the time indicator may be configured to output at least one marker with each of the at least one marker corresponding with a unit of time, such as an hour, wherein the number of markers corresponds to the maximum period between the preceding event and the subsequent event. More in particular, the controller 4 may be configured to drive the display of the time indicator 23 to adapt the number of markers in correspondence with an input to the controller for a change to the maximum period between the preceding event and the subsequent event. Thus the maximum period may be adapted to the particular needs of any individual person.

Dependent on the risk of developing pressure ulcers for a specific patient, a full circle may represent a different "real" time. If a first patient has to be moved every half an hour up to an hour, a full circle may represent half an hour, whereas for another patient that is less prone to developing pressure ulcers, a full circle may represent forty-five minutes up to 4 hours. The three markers 123 on the display of leftmost time indicator 23 in FIG. 4 provide information that the corresponding patient needs to be checked and turned every three hours. The middle indicator 23 has a single marker 123, indicating a maximum period between events of one hour, and rightmost indicator has two markers 123 for a maximum period of two hours. In this manner an intuitive reference to the maximum period is provided with the indication of the lapsed or remaining amount thereof, to assist care staff to plan their duties.

Whereas the time indicator 23 is described above in relation with the assembly 1 comprising at least one presence detector 2 and at least one liveliness detector 3, the skilled person will understand that the time indicator 23 is not limited to be used in combination with this assembly 1. Especially, the time indicator 23 may also be used with other types of detectors. The invention thus also relates to a time indicator 23 that is connected to a controller 4 that is configured to set the time indicator 23 based on a measurement signal of at least one detector, and that is configured to indicate a time lapsed since an event or a time to an event. If the time indicator is a stand-alone unit, not connected directly or indirectly to the at least one presence detector 2 and/or the at least one liveliness detector 3, the time indicator may have an input for a user to reset the lapsed or remaining time in relation to the maximum period between the preceding occurrence of an event, such as a patient changing posture or having taken his or her medicine, and the subsequent event. For example a nurse may enter a reset command via a button on the time indicator after having repositioned a patient or having made sure that the patient has taken his or her medicine.

The controller 4 may be configured to reset the time indicator 23 if the at least one detector detects a body 25 on a support 24 changing posture.

The at least one detector may comprise at least one of a presence detector 2 and a liveliness detector 3. More preferred, the at least one detector may comprise at least one of a piezo-resistive sensor 6, a piezo-electric sensor 7 and a camera 29. If it is only required to detect a change of body posture to reset the time indicator 23, a camera 29 may suffice.

Figure 6:
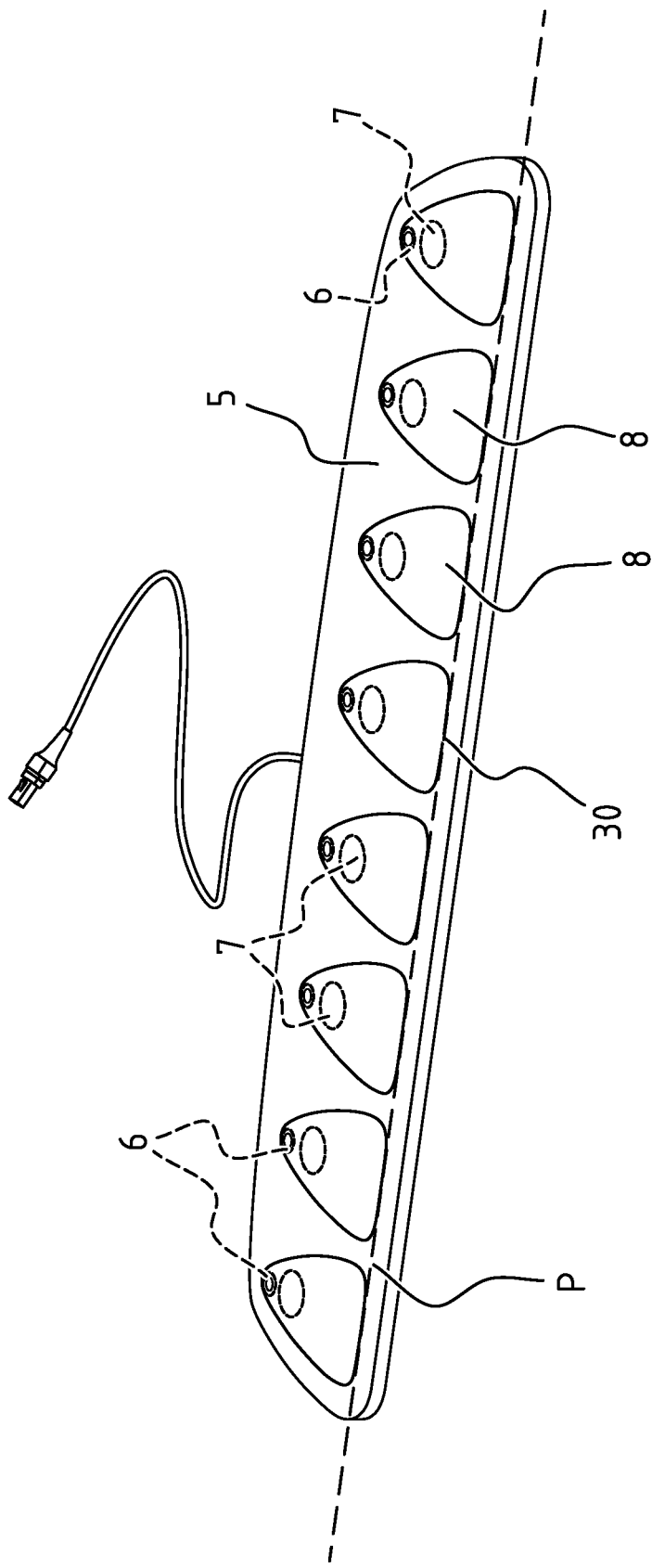
FIG. 6 is a perspective view of an assembly according to a second preferred embodiment.
Figure 7:
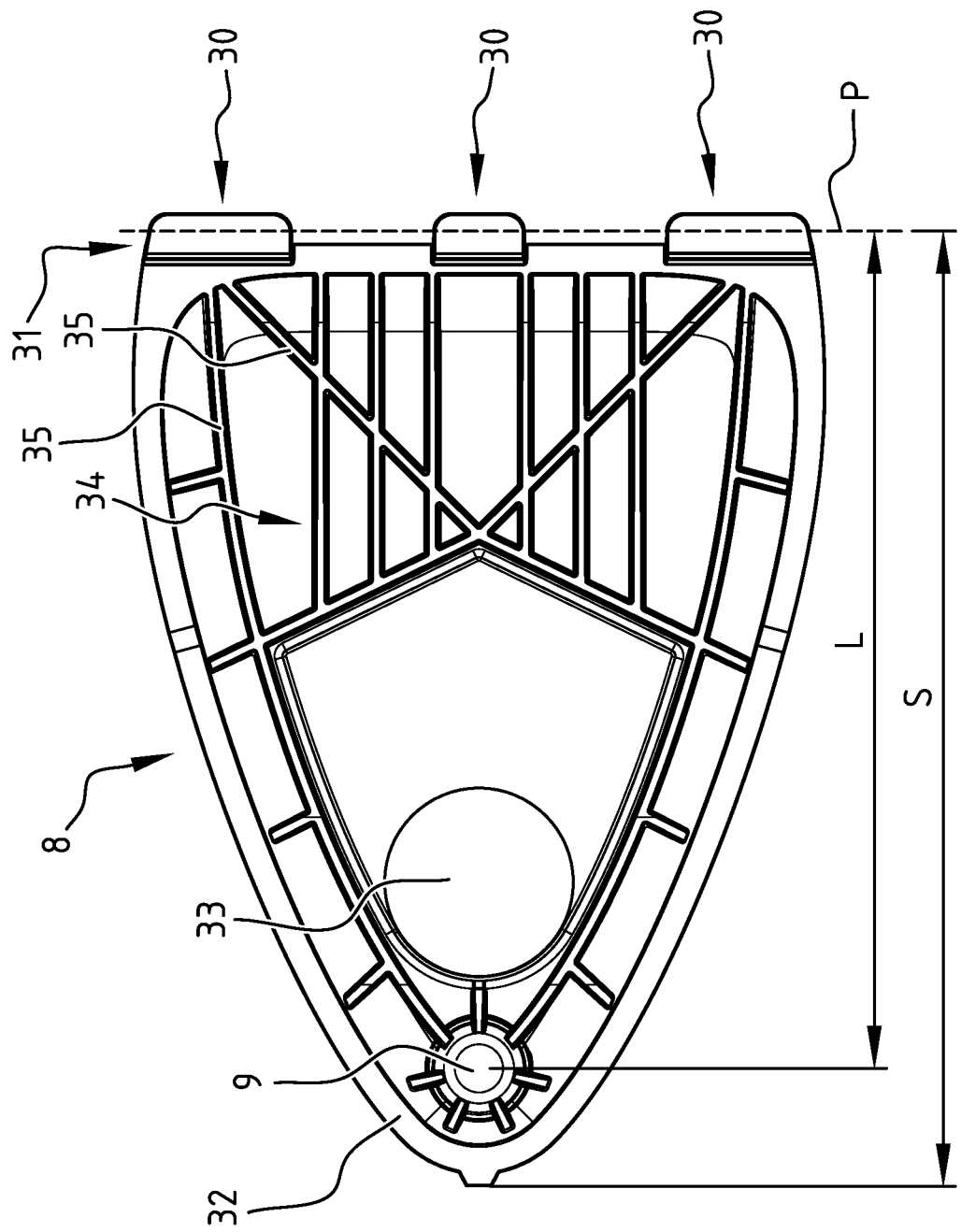
FIG. 7 is a perspective view of a concentrator of the assembly of FIG. 6.

A second preferred embodiment of an assembly 1 according to the present invention is shown in FIGS. 6 and 7. Similar reference numbers apply to the similar features as for the first embodiment. The measurement device 5 shown in FIG. 6 comprises a total of eight concentrators 8 that are pivotably arranged relative to said measurement device 5. The pivot axis P is schematically indicated.

In order to prevent unnecessary repetition, most features of the concentrators 8 that are identical to the first preferred embodiment are only briefly mentioned here. The distinguishing features are however discussed in more detail.

The concentrators 8 are again configured to concentrate a load on the presence sensor 6, of which only one is schematically shown in FIG. 6 to indicate the position thereof relative to pivot 30. Also, the concentrator 8 may be further configured to unload the presence sensor 6 in an unoccupied state of the support 24. The concentrator 8 comprises a contact portion 9 that is configured to abut the sensor 6 of the presence detector 2 when a body is present on the support 24. Preferably, the concentrator 8 is configured to have the contact portion 9 arranged at an offset relative to the sensor 6 of the presence detector 2 below a predetermined unoccupied load. This predetermined unoccupied load is preferably more than the load of an unoccupied support. The concentrator 8 may also be configured to have the contact portion 9 arranged in abutment with the sensor 6 of the presence detector 2 above a predetermined occupied load. This predetermined occupied load is less than or equal to the load of a support 24 occupied by a human body.

According to the second preferred embodiment, the concentrator 8 comprises a pivot 30 that is configured to pivotably arrange said concentrator 8 in measurement device 5. The pivot 30 is arranged at a first side 31 of the concentrator 8, and the contact portion 9 is arranged at a lever distance L from the pivot 30. The pivotable arrangement of the concentrator 8 relative to measurement device 5 in combination with the lever distance L functions as an amplifier. The longer the lever distance L to the pivot 30, the more the contact portion 9 will displace towards the presence sensor 6 at a given compressive force acting on concentrator 8. The lever distance L may therefore contribute to a more sensitive measuring of a presence of a body on the support 24 with measurement device 5.

The lever distance L is at least more than half, and preferably more than two-thirds of a size S of the concentrator 8 extending transverse to the pivot axis P of said pivot 30. As explained in the paragraph above, a longer lever distance L results in a higher amplification of a compressive force acting on the concentrator 8, and thus in a more sensitive measurement device 5. The lever distance L is therefore preferably as large a possible, i.e. the contact portion 9 is preferably arranged at or near an outer edge 32 of the concentrator 8 at a maximum distance transverse to the pivot axis P.

In the second embodiment of FIGS. 6 and 8, the concentrator 8 extends over the at least one presence sensor 6 and the at least one liveliness sensor 7, and the at least one presence sensor 6 is positioned at a greater distance from the pivot 30 than said at least one liveliness sensor 7. In this way the presence sensor 6, which may be a pressure sensor such as a piezo-resistive sensor, optimally benefits from the lever action causing the amplification.

If said concentrator 8 further comprises a resilient area 33 at or near the liveliness sensor 7. The resilient area 33 may provide a local reduced stiffness that is less than a stiffness of the contact portion 9 relative to said pivot 30. The liveliness sensor 7 may be a piezo-electric sensor.

In order to provide optimal stiffness of the concentrator 8 outside the resilient area 33, the concentrator 8 may comprise a reinforcement 34 outside the resilient area 33. The reinforcement 34 may comprise one or more than one strengthening rib 35.

For both the first and second preferred embodiment, the plurality of presence detectors 2 preferably comprises a plurality of dedicated concentrators 8.

Also, the array of sensors is, relative to the body receiving surface of the support 24, arranged at an opposite side of the support 24. In this way, the assembly 1 may be arranged e.g. under a mattress, i.e. out of sight. The arrangement at an opposite side of the support 24 relative to the body also results in an assembly 1 that is not felt by a person supported by support 24. Due to the use of the concentrators 8, a reliable measurement may still be obtained even if the array of sensors is, relative to the body receiving surface of the support 24, arranged at an opposite side of the support 24.

The above described embodiment is intended only to illustrate the invention and not to limit in any way the scope of the invention. Accordingly, it should be understood that where features mentioned in the appended claims are followed by reference signs, such signs are included solely for the purpose of enhancing the intelligibility of the claims and are in no way limiting on the scope of the claims. The scope of the invention is defined solely by the following claims.

The invention claimed is:

1. An assembly, configured to detect a body of a living person on a support having a body receiving surface configured to receive the body, and comprising:
   an array of sensors that is configured to be arranged at a distance relative to the body receiving surface of the support and comprising a plurality of presence detectors;
   a concentrator that is configured to concentrate a load on a presence sensor of one of the plurality of presence detectors in an occupied state of the support and comprising a contact portion that is configured to abut the presence sensor of the one of the plurality of presence detectors when the body is present on the support, and unload the presence sensor of the one of the plurality of presence detectors in an unoccupied state of the support,
   wherein the concentrator comprises a pivot that is configured to pivotably arrange said concentrator in a measurement device, wherein:
      the pivot is arranged at a first side of the concentrator; and
      the contact portion is arranged at a lever distance (L) from the pivot; and
   a controller configured to determine if the body is lying on a back or on a side of the body based on measurement signals of the plurality of presence detectors.

2. The assembly according to claim 1, wherein:
   the array of sensors further comprises at least one liveliness detector.

3. The assembly according to claim 2, wherein the at least one liveliness detector comprises at least one of a heart rate sensor and a breathing sensor.

4. The assembly according to claim 3, wherein:
   the at least one liveliness detector comprises both a heart rate sensor and a breathing sensor, and wherein the at least one liveliness detector is configured to sense both a heart rate pattern and a breathing pattern; and
   the controller is further configured to determine from the heart rate pattern and the breathing pattern on which of a left side and a right side of the body the living person is lying.

5. The assembly according to claim 4, wherein the controller is configured to determine a ratio between an amplitude of the heart rate pattern and an amplitude of the breathing pattern to determine on which of a left side and a right side of the body the living person is lying.

6. The assembly according to claim 2, wherein the at least one liveliness detector comprises a piezo-electric sensor.

7. The assembly according to claim 2, wherein the at least one liveliness detector comprises a force sensing sensor.

8. The assembly according to claim 2, wherein the controller is configured to determine if the body is lying on a left side or on a right side of the body based on measurement signals of the at least one liveliness detector.

9. The assembly according to claim 2, wherein:
   the concentrator extends over the presence sensor of the one of the plurality of presence detectors and the at least one liveliness detector; and
   the presence sensor of the one of the plurality of presence detectors is positioned at a greater distance from the pivot than the at least one liveliness detector.

10. The assembly according to claim 9, wherein said concentrator comprises a resilient area at the at least one liveliness detector.

11. The assembly according to claim 10, comprising a reinforcement outside the resilient area.

12. The assembly according to claim 1, wherein the plurality of presence detectors comprise at least one of a pressure sensor and a weight sensor.

13. The assembly according to claim 1, wherein the plurality of presence detectors comprise a piezo-resistive sensor.

14. The assembly according to claim 1, wherein the concentrator extends over the presence sensor of the one of the plurality of presence detectors.

15. The assembly according to claim 1, wherein at least a part of the concentrator is moveable relative to the presence sensor of the one of the plurality of presence detectors.

16. The assembly according to claim 1, wherein the concentrator is configured to have the contact portion arranged at an offset relative to the presence sensor of the one of the plurality of presence detectors below a predetermined unoccupied load.

17. The assembly according to claim 16, wherein the predetermined unoccupied load is more than a load of the support in the unoccupied state.

18. The assembly according to claim 1, wherein the concentrator is configured to have the contact portion arranged in abutment with the presence sensor of the one of the plurality of presence detectors above a predetermined occupied load.

19. The assembly according to claim 18, wherein the predetermined occupied load is less than or equal to a load of the support occupied by the body.

20. The assembly according to claim 1, wherein the lever distance (L) is at least more than half of a size of the concentrator extending transverse to a pivot axis (P) of said pivot.

21. The assembly according to claim 1, wherein the plurality of presence detectors comprises a plurality of dedicated concentrators.

22. The assembly according to claim 1, wherein the array of sensors is, relative to the body receiving surface of the support, arranged at an opposite side of the support.

23. The assembly according to claim 1, further comprising an inclination sensor configured to measure an inclination of the support.

24. The assembly according to claim 23, wherein the inclination sensor comprises an accelerometer.

25. The assembly according to claim 1, wherein the lever distance (L) is more than two-thirds of a size of the concentrator extending transverse to a pivot axis (P) of said pivot.

26. An assembly, configured to detect a body on a support having a body receiving surface configured to receive the body, and comprising:
- an array of sensors that is configured to be arranged at a distance relative to the body receiving surface of the support and comprising a plurality of presence detectors; and
- a concentrator that is configured to concentrate a load on a presence sensor of one of the plurality of presence detectors in an occupied state of the support and comprising a contact portion that is configured to abut the presence sensor of the one of the plurality of presence detectors when the body is present on the support, and unload the presence sensor of the one of the plurality of presence detectors in an unoccupied state of the support, wherein the concentrator is configured to have the contact portion arranged at an offset relative to the presence sensor of the one of the plurality of presence detectors below a predetermined unoccupied load
- wherein the concentrator comprises a pivot that is configured to pivotably arrange said concentrator in a measurement device, wherein:
- the pivot is arranged at a first side of the concentrator; and
- the contact portion is arranged at a lever distance (L) from the pivot.

* * * * *